United States Patent [19]
Arita et al.

[11] Patent Number: 5,124,331
[45] Date of Patent: Jun. 23, 1992

[54] 3,4-DIHYDROTHIENO[2,3-D]PYRIMIDINE COMPOUNDS AND THEIR PHARMACEUTICAL USE

[75] Inventors: Masafumi Arita, Tokorozawa; Yoshitaka Fukumasu, Kiyose; Mitsuharu Sano, Fukuoka; Yukio Hoshino, Kiyose; Hirotsugu Komatsu, Tokyo, all of Japan

[73] Assignee: Yoshitomi Pharmaceutical Industries, Ltd., Osaka, Japan

[21] Appl. No.: 439,044

[22] PCT Filed: Mar. 1, 1989

[86] PCT No.: PCT/JP89/00215
§ 371 Date: Nov. 2, 1989
§ 102(e) Date: Nov. 2, 1989

[87] PCT Pub. No.: WO89/08113
PCT Pub. Date: Aug. 9, 1989

[51] Int. Cl.⁵ .................. A61K 31/495; C07D 495/04
[52] U.S. Cl. .................. 514/253; 540/600; 544/115; 544/117; 544/250; 544/278; 514/232.8; 514/234.2; 514/267; 514/258
[58] Field of Search ............... 544/278, 117; 514/253

[56] References Cited

U.S. PATENT DOCUMENTS
4,146,716 3/1979 Cox et al. .................. 544/278

FOREIGN PATENT DOCUMENTS
62-132884 6/1987 Japan .

OTHER PUBLICATIONS
CA 86: 139984t, 1977.
CA 104: 129858f, 1986.
M. J. Kulshreshtha et al, Journal of Indian Chemical Society, vol. LVIII, Oct. 1981, pp. 982-984.

Primary Examiner—Cecilia Shen
Assistant Examiner—Jyothsna Venkat
Attorney, Agent, or Firm—Wenderoth, Lind & Ponack

[57] ABSTRACT

3,4-Dihydrothieno[2,3-d]pyrimidine compounds having immunoregulating and carcinostatic actions of the general formula

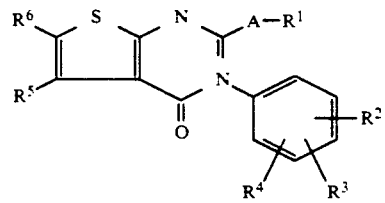

wherein A represents a $C_{1-4}$ alkylene; $R^1$ represents hydrogen, an alkyl, an aryl which may be substituted or $-N(R^7)(R^8)$; $R^2$, $R^3$ and $R^4$ represent hydrogen, a halogen, hydroxy, an alkyl which may be substituted by a halogen, an alkoxy, nitro, cyano or $-N(R^9)(R^{10})$; $R^5$ represents hydrogen, a halogen, nitro, amino, an alkyl or an alkoxycarbonyl; $R^6$ represents hydrogen, a halogen, nitro, amino, cyano, an alkyl, an alkoxycarbonyl, a halogenosulfonyl or $-SO_2N(R^{12})(R^{13})$; or $R^5$ and $R^6$ may, taken together, form a $C_{3-6}$ alkylene chain, and their pharmaceutical use.

3 Claims, No Drawings

3,4-DIHYDROTHIENO[2,3-D]PYRIMIDINE COMPOUNDS AND THEIR PHARMACEUTICAL USE

TECHNICAL FIELD

This invention relates to novel 2,3-dihydrothieno[2,3-d]pyrimidine compounds and their salts which are of use as immunoregulators, anticancer agents and so on, and to their use.

BACKGROUND ART

As for thieno[2,3-d]pyrimidine compounds, several kinds of similar compounds have already been reported. For example, in Chemical Abstracts, 79, 61411n, 3,4-dihydro-3-(2-chlorophenyl)-2,6-dimethyl-4-oxo-thieno[2,3-d]pyrimidine was synthesized as methaqualone analogue possessing a hypnotic action. Their actions, however, are weak. In Japanese Patent Application Examined Publication (Kokoku) No. 42271/1972, there are disclosed hexahydro-3-lower alkyl-[1]benzothieno[2,3-d]pyrimidin-1-one compounds which have a central nervous suppresive action, and an antiinflammatory action. In Japanese Patent Application Unexamined Publication (Kokai) No. 68197/1977, there are reported 3,4-dihydro-6-(N,N-dimethylsulfamoyl-4-oxo-thieno[2,3-d]pyrimidine as a synthetic intermediate for the compounds possessing an anti-microbial action, anti-virus action, antibacterial action and plant growth-regulating action.

In the specification of Indian Patent No. 151496, some kind of thienopyrimidine compounds usable for hyperlipidemic treatment are reported. In Drugs of the Future, vol. 10, No. 2, p 1885, it is described that 2-chloromethyl-5,6,7,8-tetrahydrobenzo[b]thieno[2,3-d]pyrimidin-4(3H)-one which is encompassed in said Indian Patent is useful as a hypolipidemic agent.

In Arch. Pharm. vol. 309, pp. 908–913 (1976), it is reported that 2-aminomethyl-3-(2-methylphenyl)-5,6,7,8-tetrahydro(1)benzothieno[2,3-d]pyrimidin-4(3H)-one compounds were synthesized as methaqualone analogues as mentioned above.

Meanwhile, the medicaments possessing an immunoregulating action have been in wide use recently for the prophylaxis or therapy of autoimmune diseases, the treatment of cancers, the amelioration of side-effects caused by anti-cancer agents, the therapy of infections diseases and so on. Particularly, as a medicament for chronic articular rheumatism which is one of the autoimmune diseases, the usefulness of the gold preparations for injections or oral administration is recognized, while such preparations have a defect of a number of side-effects. Accordingly, compounds having an excellent immunoregulating action and few side-effects have been demanded.

DISCLOSURE OF THE INVENTION

Under the foregoing situations, the present inventors conducted intensive studies for the purpose of providing excellent immunoregulators and, as a result, found that novel 2,3-dihydrothieno[2,3-d]pyrimidine compounds or their salts possessed not only remarkable immunoregulating actions but also anti-cancer actions, which culminated in the completion of the present invention.

This invention relates to 3,4-dihydrothieno[2,3-d]pyrimidine compounds of the general formula

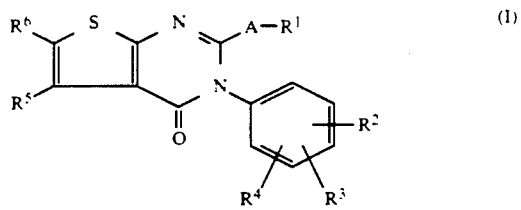

wherein A represents a straight or branched alkylene having 1 to 4 carbon atoms; $R^1$ represents hydrogen, an alkyl, an aryl which may be substituted, or a group representable by $-N(R^7)(R^8)$ wherein $R^7$ and $R^8$ are, the same or different, respectively hydrogen, an alkyl, an aralkyl which may be substituted, an aryl which may be substituted or a cycloalkyl, or $R^7$ and $R^8$ may, together with the adjacent nitrogen atom, form a ring in which nitrogen, oxygen, sulfur and $>N-R^9$ may be interposed [wherein $R^9$ represents hydrogen; an alkyl which may be substituted by hydroxy or an alkyl-substituted amino; a cycloalkyl; formyl, an aralkyl which may be substituted; an aryl which may be substituted; an arylalkenyl; a heterocyclic; an arylcarbonyl which may be substituted; or a heterocyclic carbonyl]; $R^2$, $R^3$ and $R^4$ may be the same or different and respectively represent hydrogen, a halogen, hydroxy, an alkyl which may be substituted by a halogen, an alkoxy, nitro, cyano or a group of $-N(R^{10})(R^{11})$ wherein $R^{10}$ and $R^{11}$ may be the same or different and respectively represent hydrogen, an alkyl, an alkanoyl or an arylcarbonyl which may be substituted; $R^5$ represents hydrogen, a halogen, nitro, amino, cyano, an alkyl or an alkoxycarbonyl; and $R^6$ represents hydrogen, a halogen, nitro, amino, cyano, an alkyl, an alkoxycarbonyl; a halogenosulfonyl or a group of $-SO_2N(R^{12})(R^{13})$ wherein $R^{12}$ and $R^{13}$ may be the same or different and respectively represent hydrogen, an alkyl, a cycloalkyl, an aralkyl which may be substituted, an aryl which may be substituted, an arylalkenyl or a carbonylaminoalkyl which may be substituted by an alkyl or an optionally substituted aryl, or $R^{12}$ and $R^{13}$ may, together with the adjacent nitrogen atom, form a ring in which nitrogen, oxygen, and $>N-R^{14}$ may be interposed wherein $R^{14}$ represents hydrogen, an alkyl which may be substituted by hydroxy or an alkyl-substituted by amino, a cycloalkyl, formyl, an aralkyl which may be substituted, an aryl which may be substituted, an arylalkenyl, a heterocyclic, an arylcarbonyl which may be substituted or a heterocyclic carbonyl; or $R^5$ and $R^6$ may, taken together, form an alkylene chain having 3 to 6 carbon atoms and $R^1$ represents $-N(R^7)(R^8)$ (wherein $R^7$ and $R^8$ are of the same meaning as defined above) provided that when $R^6$ represents hydrogen, a halogen, nitro, amino, cyano, an alkyl or an alkoxycarbonyl or $R^5$ and $R^6$, taken together, form an alkylene chain having 3 to 6 carbon atoms, and when $R^5$ and $R^6$, taken together, form an alkylene chain having 3 to 6 carbon atoms, $R^2$, $R^3$ and $R^4$ represent one of the groups as defined above other than an alkyl, or a salt thereof and to an immunoregulator or an anti-cancer agent which is characterized by containing, as the active ingredient, a compound of the general formula

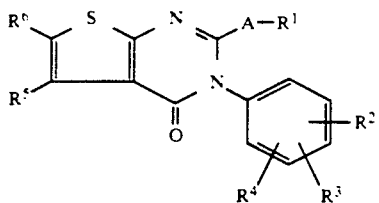

wherein A represents a straight or branched alkylene having 1 to 4 carbon atoms; $R^1$ represents hydrogen, an alkyl, an aryl which may be substituted, or a group representable by $-N(R^7)(R^8)$ wherein $R^7$ and $R^8$ are, the same or different, respectively hydrogen, an alkyl, an aralkyl which may be substituted, an aryl which may be substituted or a cycloalkyl, or $R^7$ and $R^8$ may, together with the adjacent nitrogen atom, form a ring in which nitrogen, oxygen, sulfur and $>N-R^9$ may be interposed [wherein $R^9$ represents hydrogen; an alkyl which may be substituted by hydroxy or an alkyl-substituted amino; a cycloalkyl; formyl, an aralkyl which may be substituted; an aryl which may be substituted; an arylalkenyl; a heterocyclic; an arylcarbonyl which may be substituted; or a heterocyclic carbonyl]; $R^2$, $R^3$ and $R^4$ may be the same or different and respectively represent hydrogen, halogen, hydroxy, an alkyl which may be substituted by a halogen, an alkoxy, nitro, cyano or a group of $-N(R^{10})(R^{11})$ wherein $R^{10}$ and $R^{11}$ may be the same or different and respectively represent hydrogen, an alkyl, an alkanoyl or an arylcarbonyl which may be substituted; $R^5$ represents hydrogen, a halogen, nitro, amino, cyano, an alkyl or an alkoxycarbonyl; and $R^6$ represents hydrogen, a halogen, nitro, amino, cyano, an alkyl, an alkoxycarbonyl; a halogenosulfonyl or a group of $-SO_2N(R^{12})(R^{13})$ wherein $R^{12}$ and $R^{13}$ may be the same or different and respectively represent hydrogen, an alkyl, a cycloalkyl, an aralkyl which may be substituted, an aryl which may be substituted, an arylalkenyl or a carbonylaminoalkyl which may be substituted by an alkyl or an optionally substituted aryl, or $R^{12}$ and $R^{13}$ may, together with the adjacent nitrogen atom, form a ring in which nitrogen, oxygen, and $>N-R^{14}$ may be interposed wherein $R^{14}$ represents hydrogen, an alkyl which may be substituted by hydroxy or an alkyl-substituted amino, a cycloalkyl, formyl, an aralkyl which may be substituted, an aryl which may be substituted, an arylalkenyl, a heterocyclic, an arylcarbonyl which may be substituted or a heterocyclic carbonyl; or $R^5$ and $R^6$ may, taken together, form an alkylene chain having 3 to 6 carbon atoms or a salt thereof.

Below, the above-mentioned definitions are in further detail explained respectively.

With respect to A, the straight or branched alkylene having 1 to 4 carbon atoms is exemplified by methylene, ethylene, trimethylene, tetramethylene, propylene and isopropylidene.

With respect to $R^1$, the alkyl means a straight or branched alkyl, preferably, having 1 to 5 carbon atoms (e.g. methyl, ethyl, propyl, isopropyl, butyl, tert-butyl, pentyl), As for $R^1$, the aryl which may be substituted means a phenyl which may be substituted by, preferably, an alkyl having 1 to 4 carbon atoms such as methyl, ethyl, etc., a halogen (chlorine, bromine, fluorine, etc.) and/or an alkoxy having 1 to 4 carbon atoms such as methoxy or ethoxy.

With respect to $R^7$ and $R^8$ in $-N(R^7)(R^8)$, the alkyl means a straight or branched alkyl, preferably, having 1 to 4 carbon atoms, which may be exemplified by methyl, ethyl, propyl, isopropyl, butyl, tert-butyl, etc.

As for $R^7$ and $R^8$, the cycloalkyl means a cycloalkyl, preferably, having 3 to 7 carbon atoms, which is exemplified by cyclopentyl, cyclohexyl, cycloheptyl, etc.

As for $R^7$ and $R^8$, the aryl means an aryl, preferably, having 6 to 10 carbon atoms, which may be substituted by an alkoxy (e.g. an alkoxy having 1 to 4 carbon atoms such as methoxy or ethoxy), a halogen (e.g. fluorine, chlorine) which is exemplified by phenyl, p-methoxyphenyl, o-chlorophenyl, etc.

As for $R^7$ and $R^8$, the aralkyl means an aralkyl having an aryl, preferably, having 6-10 carbon atoms and an alkyl having, preferably, 1 to 4 carbon atoms, which may be substituted by an alkyl (an alkyl having 1 to 4 carbon atoms such as methyl or ethyl) etc. Such aralkyls may be exemplified by benzyl, p-methylbenzyl, 2-phenylethyl, etc.

When $R^7$ and $R^8$, together with the adjacent nitrogen atom, form a ring, the ring is preferably 4- to 8-membered ring, which may be saturated or unsaturated. As such rings, mention is made of, for example, 1-pyrrolyl, 1-pyrrolidinyl, piperidino, homopiperidino and the like. Further, nitrogen, oxygen, sulfur and $>N-R^9$ may be optionally interposed in the ring. Such rings may be exemplified by 1-piperazinyl, 1homopiperazinyl, 1-imidazolyl, 1-triazolyl, morpholino, thiomorpholino and thiazolidinyl.

With respect to $R^9$, the alkyl means a straight or branched alkyl having, preferably, 1 to 6 carbon atoms, which is exemplified by methyl, ethyl, propyl, isopropyl, butyl, isobutyl, pentyl and hexyl. The alkyl may be substituted by hydroxy, and as such groups, mention may be made of hydroxymethyl, 2-hydroxyethyl and 2-hydroxypropyl. As the mono- or di-alkylamine-substituted alkyl, mention may be made of mono- or dialkylaminoalkyl, wherein the alkyl by which the amino is substituted is usually an alkyl having 1 to 4 carbon atoms. Such mono- or di-alkylaminoalkyls are exemplified by 2-methylaminoethyl, 2-diethylaminoethyl and 3-dimethylaminopropyl.

With respect to $R^9$, the cycloalkyl is a cycloalkyl having, preferably, 3 to 6 carbon atoms, which is exemplified by cyclopropyl, cyclopentyl and cyclohexyl.

With respect to $R^9$, the aryl is an aryl having, preferably, 6 to 10 carbon atoms, which may be substituted by an alkyl (an alkyl having 1 to 4 carbon atoms such as methyl or ethyl), an alkoxy (an alkoxy having 1 to 4 carbon atoms such as methoxy or ethoxy), a halogen (e.g. fluorine, chlorine), etc., which aryl is exemplified by o-methoxyphenyl, 2,4-dimethoxyphenyl, p-tolyl, p-chlorophenyl and 3,4-difluorophenyl.

With respect to $R^9$, the aralkyl has an alkyl having, preferably, 1 to 3 carbon atoms and an aryl having, preferably, 6 to 10 carbon atoms, and may be substituted by a halogen (e.g. fluorine, chlorine), halogenoalkyl (e.g. trifluoromethyl), etc. Such aralkyls are exemplified by benzyl, p-chrolobenzyl, m-trifluoromethylbenzyl, o-fluorobenzyl, 2-phenylethyl and 3-phenylpropyl.

With respect to $R^9$, the arylalkenyl has a straight or branched alkenyl having, preferably, 2 to 4 carbon atoms and an aryl having, preferably, 6 to 10 carbon atoms, and as such arylalkenyls, mention is made of, for example, cinnamyl.

With respect to $R^9$, the arylcarbonyl means an arylcarbonyl having an aryl of, preferably, 6 to 10 carbon atoms which may be substituted by hydroxy, a halogen (e.g. fluorine, chlorine), etc., which arylcarbonyl is exemplified by benzoyl, p-chlorobenzoyl and o-hydroxybenzoyl.

With respect to $R^9$, the heterocyclic of the heterocyccliccarbonyl is a saturated or unsaturated heterocyclic containing 1 or 2 hetero atoms such as nitrogen, oxygen and/or sulfur and may be a condensed ring of 2 or more rings. Such heterocycliccarbonyls are exemplified by 2-furoyl, 2-thenoyl and nicotinoyl.

With reference to $R^2$, $R^3$ and $R^4$, the halogen means fluorine, chlorine, bromine and iodine. The alkyl which may be substituted by a halogen is a straight or branched alkyl having, preferably, 1 to 4 carbon atoms, which is exemplified by methyl, ethyl, propyl, isopropyl, butyl, tert-butyl and trifluoromethyl. The alkoxy means an alkoxy having, preferably, 1 to 4 carbon atoms, which is exemplified by methoxy, ethoxy and propoxy.

With reference to $R^{10}$ and $R^{11}$ of $-N(R^{10})(R^{11})$, the alkyl means a straight or branched alkyl having, preferably, 1 to 4 carbon atoms, which is exemplified by methyl, ethyl, propyl, isopropyl, butyl and tert-butyl.

With reference to $R^{10}$ and $R^{11}$, the alkanoyl means a straight or branched alkanoyl having, preferably, 2 to 5 carbon atoms, which is exemplified by acetyl, propionyl, butyryl and pivaloyl.

With reference to $R^{10}$ and $R^{11}$, the arylcarbonyl has an aryl having, preferably, 6 to 10 carbon atoms which may be substituted by a halogen (e.g. fluorine, chlorine), which arylcarbonyl is exemplified by benzoyl and p-chlorobenzoyl.

With reference to $R^5$, the alkyl means a straight or branched alkyl having, preferably, 1 to 4 carbon atoms, which is exemplified by methyl, ethyl, propyl, isopropyl, butyl and tert-butyl.

With reference to $R^5$, the alkoxycarbonyl has a straight or branched alkoxy having, preferably, 1 to 4 carbon atoms, which alkoxycarbonyl is exemplified by methoxycarbonyl, ethoxycarbonyl, propoxycarbonyl, isopropoxycarbonyl, butoxycarbonyl and tert-butoxycarbonyl.

With reference to $R^6$, the alkyl means a straight or branched alkyl having, preferably, 1 to 4 carbon atoms, which is exemplified by methyl, ethyl, propyl, isopropyl, butyl and tert butyl.

With reference to $R^6$, the alkoxycarbonyl has a straight or branched alkoxy having, preferably, 1 to 4 carbon atoms, which alkoxycarbonyl is exemplified by methoxy carbonyl, ethoxycarbonyl, propoxycarbonyl, isopropoxycarbonyl, butoxycarbonyl and tert-butoxycarbonyl.

With reference to $R^6$, the halogen in the halogenosulfonyl means fluorine, chlorine, bromine or iodine, and as such halogenosulfonyls, mention is made of, for example, chlorosulfonyl.

With reference to $R^{12}$ and $R^{13}$ of $-SO_2N(R^{12})(R^3)$, the alkyl means a straight or branched alkyl having, preferably, 1 to 4 carbon atoms, which is exemplified by methyl, ethyl, propyl, isopropyl, butyl and tert-butyl.

With reference to $R^{12}$ and $R^{13}$, the cycloalkyl means a cycloalkyl having, preferably, 3 to 7 carbon atoms, which is exemplified by cyclopropyl, cyclopentyl, cyclohexyl, and cycloheptyl.

With reference to $R^{12}$ and $R^{13}$, the aryl may be substituted by an alkyl (an alkyl having 1 to 4 carbon atoms such as methyl or ethyl), an alkoxy (an alkoxy having 1 to 4 carbon atoms such as methoxy or ethoxy) and a halogenoalkyl (e.g. trifluoromethyl), and the aryl is an aryl having, preferably, 6 to 10 carbon atoms, which is exemplified by phenyl, p-methoxyphenyl, p-tolyl and m-trifluoromethylphenyl.

With reference to $R^{12}$ and $R^{13}$, the aralkyl has an alkyl having, preferably, 1 to 3 carbon atoms and an aryl having, preferably, 6 to 10 carbon atoms, and the aralkyl may be substituted by a halogen (fluorine, chlorine, etc.), etc. As such an aralkyl, mention is made of, for example, benzyl and p-fluorobenzyl.

With reference to $R^{12}$ and $R^{13}$, the arylalkenyl has a straight or branched alkenyl having, preferably, 2 to 4 carbon atoms and an aryl having, preferably, 6 to 10 carbon atoms, which arylalkenyl is exemplified by cinnamyl.

With reference to $R^{12}$ and $R^{13}$, the alkyl-substituted carbonyl of the alkyl-substituted carbonylaminoalkyl means a straight or branched alkanoyl having, preferably, 2 to 5 carbon atoms and the alkyl means a straight or branched alkyl having, preferably, 1 to 6 carbon atoms. As such alkyl-substituted carbonylaminoalkyls, mention is made of, for example, 2-acetylaminoethyl, 4-acetylaminobutyl and 6-propionylaminohexyl. The aryl of the aryl-substituted carbonylaminoalkyl may be substituted by a halogen (e.g. fluorine, chlorine). The aryl thereof is an aryl having, preferably, 6 to 10 carbon atoms, and the alkyl thereof is a straight or branched alkyl having, preferably, 1 to 6 carbon atoms as mentioned above. As such groups, mention can be made of, for example, 4-benzoylaminobutyl and 6-(p-chlorobenzoyl)aminohexyl.

When $R^{12}$ and $R^{13}$, together with the adjacent nitrogen atom, form a ring, the ring is preferably 4- to 8-membered, saturated or unsaturated, ring. As such rings, mention may be made of, for example, 1-pyrrolyl, 1-pyrrolidinyl, piperidino and homopiperidino. Further, nitrogen, oxygen, sulfur and $>N-R^{14}$ may be interposed in said ring. As such rings, mention may be made of, for example, 1-piperazinyl, 1-homopiperazinyl, 1-imidazolyl, 1-triazolyl, morpholino, thiomorpholino and thiazolidinyl.

With reference to $R^{13}$, as the alkyl which may be substituted by an alkyl-substituted amino, the cycloalkyl, the aryl which may be substituted, the aralkyl which may be substituted, the arylalkenyl, the heterocyclic, the formyl, the arylcarbonyl which may be substituted and the heterocyclic, there may be mentioned the same ones as the groups mentioned above with respect to $R^8$ respectively.

The alkylene chain having 3 to 6 carbon atoms formed by $R^5$ and $R^6$, taken together forms, together with the thiophene ring, cyclopentathiophene ring, tetrahydrobenzothiophene ring or cycloheptathiophene ring.

As the salts of the compounds of the formula (I) of the present invention, preferred are pharmaceutically acceptable acid addition salts of an inorganic acid such as hydrochloric acid, hydrobromic acid or sulfuric acid and those of an organic acid such as oxalic acid, fumaric acid, maleic acid, mandelic acid, citric acid, tartaric acid or salicylic acid. Also, their hydrates (1 hydrate, ½ hydrate, ¼ hydrate, etc.) are encompassed in the present invention.

In the case of the compounds having a chiral carbon atom, among the compounds of the formula (I) of the present invention, the optical isomers thereof are also included in the present invention.

Among the compounds of the formula (I) of the present invention, preferable are the compounds of the formula (I) wherein $R^6$ represents $-SO_2N(R^{12})(R^{13})$ wherein $R^{12}$ and $R^{13}$ are as defined above and the compounds wherein $R^6$ represents hydrogen, a halogen, nitro, amino, cyano, an alkyl or an alkoxycarbonyl or $R^5$ and $R^6$, taken together, form an alkylene chain having 3 to 6 carbon atoms and $R^1$ represents $-N(R^7)(R^8)$ wherein $R^7$ and $R^8$ are as defined above. Furthermore, more preferable compounds are the compounds selected from among 3,4-dihydro-3-(2-chlorophenyl)-2-(4-ethyl-1-piperazinyl)methyl-4-oxo-6-sulfamoyl-thieno[2,3-d]pyrimidine; 3,4-dihydro-3-(2-chlorophenyl)-2-(4-ethyl-1-piperazinyl)methyl-5,6-dimethyl-4oxothieno[2,3-d]pyrimidine; 3,4,5,6,7,8-hexahydro-3-(2-chlorophenyl)-2-(4-ethyl-1-piperazinyl)methyl-4-oxo(1)benzothieno[2,3-d]pyrimidine; 3,4-dihydro-3-(2-chlorophenyl)-6-ethoxycarbonyl-2-(4-ethyl-1-piperazinyl)methyl-5-methyl-4oxothieno[2,3-d]pyrimidine; 3,4-dihydro-3-(2-chlorophenyl)-2-methyl-4-oxo-6-sulfamoylthieno[2,3-d]pyrimidine; 3,4-dihydro-3-(2-chlorophenyl)-6-ethyl-2-(4-ethyl-1-piperazinyl)methyl-4-oxothieno[2,3-d]pyrimidine; 3,4-dihydro-3-(2-fluorophenyl)-2-(4-methyl-1-piperazinyl)methyl-4-oxo-6-sulfamoylthieno[2,3-d]pyrimidine; 3,4-dihydro-3-(2-chlorophenyl)-2-morpholinomethyl-4-oxo-6-sulfamoyl-thieno[2,3-d]pyrimidine; 3,4-dihydro-6-bromo-3-(2-chlorophenyl)-2-(4-ethyl-1-piperazinyl)methyl-4-oxothieno[2,3-d]pyrimidine; 3,4-dihydro-6-chloro-3-(2-chlorophenyl)-2-(4-ethyl-1-piperazinyl)methyl-4-oxothieno[2,3-d]pyrimidine; 3,4-dihydro-3-(2-chloro-4-nitrophenyl)-2-(4-ethyl-1-piperazinyl)methyl-6-nitro-4-oxothieno[2,3-d]pyrimidine; and 3,4-dihydro-3-(2-chlorophenyl)-2-(4-methyl-1-piperazinyl)methyl-4-oxo-6-sulfamoylthieno[2,3-d]pyrimidine and their salts and hydrates.

The compounds of the formula (I) of the present invention can be produced, for example, by the following method.

METHOD 1

By reacting a compound of the formula (II)

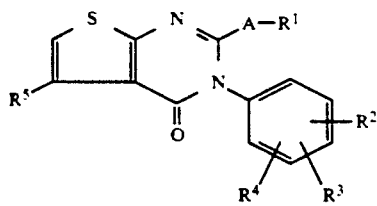

(II)

wherein A, $R^1$, $R^2$, $R^3$, $R^4$ and $R^5$ are of the same meaning as mentioned above, with a halogenosulfonic acid (especially, chlorosulfonic acid) or a halogenosulfuryl (especially, sulfuryl chloride) or alternatively by sulfonating a compound of the formula (II) followed by halogenation, the compound of the formula (III)

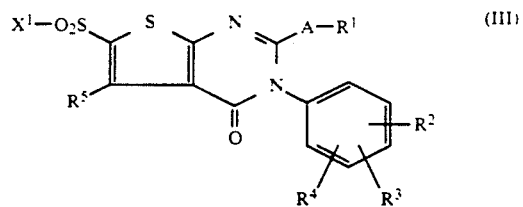

(III)

wherein $X^1$ represents a halogen, and A, $R^1$, $R^2$, $R^3$, $R^4$ and $R^5$ are of the same meaning as defined above; can be produced.

This reaction can be conducted, for example, in the following manner.

① The compound of the formula (II) is reacted with chlorosulfonic acid without solvent or in an organic solvent such as chloroform and carbon tetrachloride at a temperature ranging from room temperature to 100° C. (preferably 70°–100° C.); ② the compound of the formula (II) is reacted with sulfuryl chloride in an organic solvent such as tetrahydrofuran or hexane, or ③ the compound of the formula (II) is heated with fuming sulfuric acid or 95% sulfuric acid-acetic anhydride at 70°–100° C. and then treated with a base to obtain a sulfonate (sodium salt, potassium salt, etc.), which is heated (100°–200° C.) with phosphorus pentachloride or phosphorus oxychloride.

The compound of the formula (II) can be produced by the methods as described in Chemical Abstracts, 79, 61411n, M. S. Mankas et al (J. Med. Chem. 15, 106 (1972)) and so on.

METHOD 2

The compound of the formula (III) can be also produced by the following method.

① A compound of the formula (II) is subjected to nitration to obtain the compound of the formula (IV)

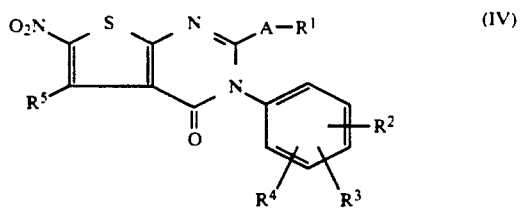

(IV)

wherein A, $R^1$, $R^2$, $R^3$, $R^4$ and $R^5$ are as defined above.

Said nitration reaction can be conducted by the per se known method, for example, by a method of heating at 50°–60° C. with nitric acid in the presence of sulfuric acid, by a method of reacting with nitric acid-acetic anhydride at a lowered temperature, by a method of using fuming nitric acid-glacial acetic acid or by other methods ② A compound of the formula (IV) is reduced to obtain the compound of the formula (V)

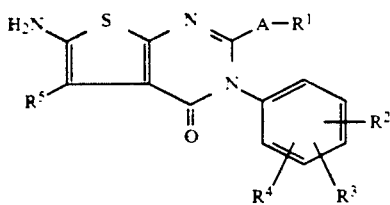

wherein A, $R^1$, $R^2$, $R^3$, $R^4$ and $R^5$ are as defined above.

As said reduction, mention can be made of, for example, reduction under acidic conditions (with zinc, iron, stannous chloride or the like together with acetic acid, conc. hydrochloric acid or the like), reduction with a sulfide (a method of heating under reflux with sodium sulfide, sodium polysulfide, sodium hydrogensulfide, sodium thiosulfate, ammonium sulfide, etc. in a hydrous alcohol solvent), a method of hydrogenation using a catalyst such as Raney nickel, 10% palladium/carbon, palladium oxide, etc.

③ A compound of the formula (V) is diazotization, followed by treatment with a cupric halogenide-sulfur dioxide to obtain the compound of the formula (III).

That is, by reacting the compound of the formula (V) with sodium nitrite, a strong acid (sulfuric acid, conc. hydrochloric acid, hydrobromic acid, etc.) and a weak acid (acetic acid, etc.) at 0°–5° C. to produce diazoniun salt, which is added in a solution of a cupric halogenide (cupric chloride, cupric bromide, etc.) and sulfur dioxide in acetic acid to obtain the compound of the formula (III), for example, 6-chlorosulfonyl-substituted compound, 6-bromosulfonyl-substituted compound and the like.

METHOD 3

A compound of the formula (III) is reacted with a compound of the formula (VI)

wherein $R^{12}$ and $R^{13}$ are as defined above to produce the compound of the formula (VII)

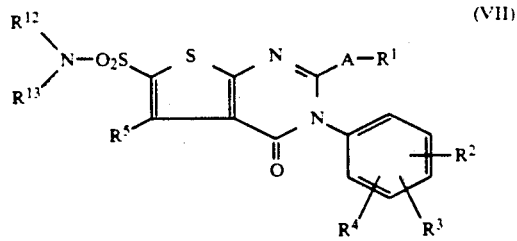

wherein A, $R^1$, $R^2$, $R^3$, $R^4$, $R^5$, $R^{12}$ and $R^{13}$ are as defined above.

This reaction can be carried out, preferably, in water or an organic solvent such as chloroform, methylene chloride tetrahydrofuran, dioxane, acetonitrile, ether, ethyl acetate, benzene, toluene, dimethylformamide, dimethylsulfoxide or so on, or a mixed solvent thereof. Besides, this reaction can be carried out in the presence of a suitable organic base (triethylamine, pyridine, dimethylaminopyridine, diisopropylethylamine, etc.) or an inorganic base (potassium carbonate, sodium carbonate, sodium hydrogencarbonate, etc.). The reaction temperature is preferably in the range from $-20°$ C. to the boiling point of the solvent used.

METHOD 4

A compound of the formula (VIII)

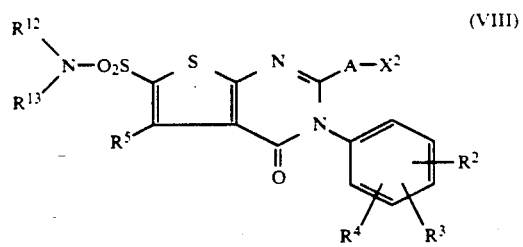

wherein $X^2$ is a halogen, and A, $R^2$, $R^3$, $R^4$, $R^5$, $R^{12}$ and $R^{13}$ are as defined above is reacted with a compound of the formula (IX)

wherein $R^7$ and $R^8$ are as defined above to produce the compound of the formula (X)

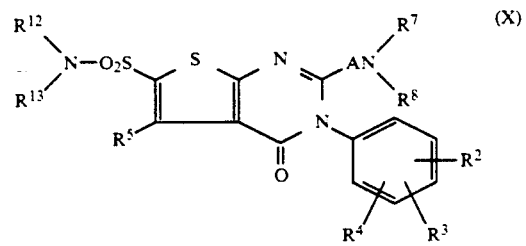

wherein A, $R^2$, $R^3$, $R^4$, $R^5$, $R^7$, $R^8$, $R^{12}$ and $R^{13}$ are as defined above.

Said reaction can be usually carried out in the presence of an organic base (triethylamine, pyridine, dimethylaminopyridine, diisopropylethylamine, etc.) or an inorganic base (potassium carbonate, sodium carbonate, sodium hydrogencarbonate, etc.) in a suitable solvent (water, acetone, chloroform, tetrahydrofuran, acetonitrile, dimethylformamide, etc., or a mixed solvent thereof) at 0°–80° C.

The compound of the formula (VIII) can be produced by reacting the compound of the formula (VII) (wherein $R^1$ represents hydrogen or an alkyl) with a halogenating agent such as N-bromosuccinimide, N-chlorosuccinimide, bromine, chlorine or fluorine.

This halogenation reaction can be conducted usually in the presence of a peroxide (dibenzoyl peroxide, m-chloroperbenzoic acid, t-butyl hydroperoxide, peracetic acid, etc.) or azoisobutyronitrile (AIBN) in an organic solvent such as acetic acid, carbon tetrachloride, chloroform, benzene, toluene, dimethylformamide, etc., or with photoirradiation.

METHOD 5

① A compound of the formula (II) is reacted with a halogenating agent such as N-bromosuccinimide, N- chlorosuccinimide. bromine, chlorine. fluorine, etc. to produce the compound of the formula (XI)

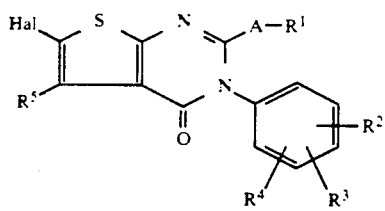

wherein Hal represents chlorine, bromine or fluorine and A, $R^1$, $R^2$, $R^3$, $R^4$ and $R^5$ are as defined above.

The halogenation reaction proceeds under the conditions as described in Method 4.

(2) A compound of the formula (XI) is treated with cuprous cyanide at 150°-250° C. in an organic solvent such as dimethylformamide or pyridine to produce the compound of the formula (XII)

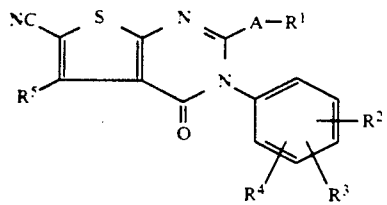

wherein A, $R^1$, $R^2$, $R^3$, $R^4$ and $R^5$ are as defined above.

A compound of the formula (XIII)

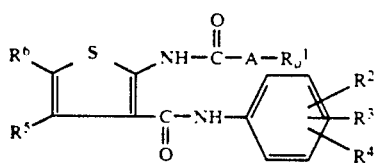

wherein $R^1_a$ represents hydrogen, a halogen, an alkyl or an aryl, and $R^2$, $R^3$, $R^4$, $R^5$ and $R^6$ are as defined above is subjected to ring-closure reaction, or in case of a compound of the formula (XIII) wherein $R^1_a$ is a halogen, the compound is reacted with a compound of the formula (IX), followed by ring-closure reaction to produce the compound of the formula (I).

This ring-closure reaction can be conducted by heating, under reflux, the compound of the formula (XIII) in the presence of phosphorus oxychloride, phosphorus oxybromide, phosphorus trichloride, phosphorus tribromide, thionylchloride and the like in a solvent such as anhydrous benzene, anhydrous toluene, anhydrous xylene, etc.

The reaction of the compound wherein $R^1_a$ is a halogen with the compound of the formula (IX) can be carried out in the same manner as in Method 4.

A compound of the formula (XII) can be produced by reacting a compound of the formula (IV')

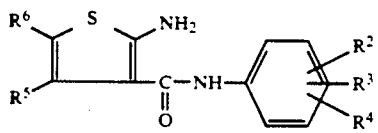

wherein $R^2$, $R^3$, $R^4$, $R^5$ and $R^6$ are as defined above with a compound of the formula (XV)

$$R^1_a-ACOOH \qquad (XV)$$

wherein $R^1_a$ is as defined above, or its reactive derivative.

As the reactive derivatives of the compound of the formula (XV), mention is made of acid halides, acid anhydrides, active amines, active esters, nitriles, etc. As the compounds of the formula (XV) or their reactive derivatives, mention is made of, for example, acid halides (acetyl chloride, chloroacetyl chloride, etc.), acetoniles (chloroacetonitrile, bromoacetonitrile, etc.) acetamides (chloroacetamide), etc.

This reaction can be conducted by reacting in the presence of a base (triethylamine, pyridine, diisopropylethylamine, etc.) in a suitable solvent (chloroform, methylene chloride, toluene, benzene, etc.) at 0°-50° C.

METHOD 7

A compound of the formula (XVI)

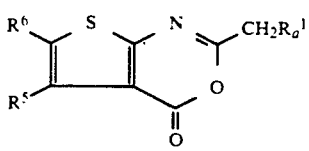

wherein $R^1_a$, $R^5$ and $R^6$ are of the same meaning as defined above is subjected to ring-closure reaction in the co-existence with a substituted aniline of the formula (XVII)

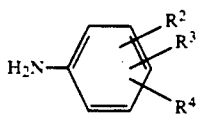

wherein $R^2$, $R^3$ and $R^4$ are of the same meaning as defined above or in case of the compound of the formula (XVI) wherein $R^1_a$ is a halogen, the compound is reacted with a compound of the formula (IX) to obtain the compound of the formula (I).

This reaction can be conducted by heating under reflux with phosphorus oxychloride, phosphorus trichloride, thionyl chloride and so on. The reaction temperature in the reaction with the compound of the formula (IX) is the same as in Method 4. The reaction temperature is, preferably, 30°-70° C.

The compounds of the formula (I) can be converted into the pharmaceutically acceptable salts thereof by the per se known methods. Also, the salts can be converted into the free compounds by the per se known methods.

Among the compounds of the formula (I), the compounds having chiral carbon atoms, can be obtained generally as a racemic body, which can be resolved by the conventional method to give their optically active isomers. The optically active isomers can also be synthesized by using the optically active starting compounds.

The compounds of the formula (I) and their pharmaceutically acceptable salts of the present invention possess immuno regulating actions such as antibody-production-suppressive actions and delayed hypersensitive reaction potentiating actions and anti-cancer actions against mammals such as humans, cattles, horses, dogs, mice, rats, etc., and therefore are useful as the prophylactic or therapeutic agents for systemic (organ-non-specific) autoimmune diseases such as chronic articular rheumatism, systemic lupus erythematosus, scleroderma, polymyositis, dermatomyositis, mixed fibrositis, nodose periarteritis and necrotic angititis; autoimmune diseases, and organ-specific autoimmune diseases such as autoimmune thyroid gland diseases, autoimmune diabetes, grave myoasthenia, Sjogren's syndrome (diseases), anti-GBM antibody disease (autoimmune nephritis) autoimmune cardiac diseases, autoimmune blood diseases and autoimmune hepatic diseases, immunosuppressive agents in skin, marrow and other various internal organs transplantation in human and other various mammals, or anti-cancer agents.

PHARMACOLOGICAL EXPERIMENTAL EXAMPLE 1

Inhibitory Effect on Antibody Production

Using male MRL/1 mice (6 individuals per group), for 4 weeks from 12 weeks old to 15 weeks old, the test compounds suspended in 0.5% methyl cellulose were orally administered (at the dose of 10 mg/kg), and at the time of 16 weeks old, the serum was obtained from the blood collected in the eyeground. The contents of IgG, IgM, Anti-ssDNA antibody and IgM-rheumatoid factor were measured in accordance with the standard ELISA method, and the suppressive rate (%) relative to the control group was calculated. The results are tabulated in Table 1. By continuing the administration to the test animals thereafter and confirming the death dates of the animals, the mean survival days were estimated (in Table, taking the survival days of the control group as 100%, the relative rates of the survival days of the test groups are shown). To the control group, 0.5% methyl cellulose was intraperitoneally administered for the same period.

TABLE 1

| Compound No. | Serum Antibody Levels (Suppressive rate, %) | | | | Mean survival days |
|---|---|---|---|---|---|
| | IgG (mg/ml) | IgM (mg/ml) | Anti-DNA-antibody (U/ml) | IgM-rheumatoid factor (U/ml) | |
| Example 2 | 70.0 | 75.8 | 79.4 | 49.5 | 127 |
| Example 11 | 50.4 | 90.9 | 76.8 | 32.6 | 115 |

As shown in Table 1, the compounds of the present invention exhibited an inhibitory effect on the production of the antibodies which increases along with aging in autoimmune disease-model MRL/1 mice through per os administration. Also, it was confirmed that the compounds displayed a tendency to prolong the survival time.

PHARMACOLOGICAL EXPERIMENTAL EXAMPLE 2

Action on Adjuvant Arthritis (a) Prophylactic Experiment

Non-viable tubercle bacilli ($R_{35}H_5$ type) suspended in liquid paraffin as the adjuvant were intracutaneously inoculated at 0.5 mg/0.1 ml to male Lewis rats (supplied by Seiwa Experimental Animal) at the age of 8–10 weeks, 8 rats per group, in the cauda root. The test compounds were orally administered once a day from the day of sensitization to the 21st day. The volume of the foot was measured by way of Water-Substitution method just before the inoculation of the adjuvant and the 10th, 15th, 18th, 21st and 28th days after the inoculation, and the assessment of the effect was conducted by estimating the variation value at the prescribed time based upon the volume of the foot before the inoculation of the adjuvant and calculating significant difference as compared with that of the control group by means of single disposal diffusion analytical method. The suppressive rate was estimated from the variation value on the 21st day. As the result, the compounds of Example 2 and Example 11 showed the suppressive rate of 34.6% and 55.3% respectively by the oral administration thereof at the dose of 30 mg/kg.

(b) Therapeutic Experiment

The animals which were sensitized in the same manner as in (a) and showed crisis of arthritis on the 15th day were selected. Each group consisted of seven animals. The test compounds were orally administered once a day from the 15th day to the 30th day. The assessment of the effect was conducted by estimating the suppressive rate relative to that of the control group from the variation value on the 30th day based upon the volume of the foot on the 15th day. As the result, the compound of Example 2 showed the suppressive rate of 95.0% by the administration at the dose of 10 mg/kg and 139.6% by that at the dose of 30 mg/kg, and the compound of Example 11 showed the suppressive rate of 124.8% by the administration at the dose of 10 mg/kg and 132.7% by that at the dose of 30 mg/kg.

PHARMACOLOGICAL EXPERIMENTAL EXAMPLE 3

Action on Rat Collagen Arthritis (a) Prophylactic Experiment

Male Sprague-Dawley rat weighing 150–200 g were intracutaneously administered with 1 ml of an emulsion of II type collagen (a 1:1 emulsion of 2 mg/ml of 0.1N acetic acid and Freund's incomplete adjuvant) at 5 separate sites in the depilated back and administered with 0.2 ml of said emulsion in the cauda root 7 days after for re-sensitization. The test compounds were orally administered once a day from the day of the sensitization to the 27th day. The significance relative to the control group was studied by measuring the volume of the foot with the lapse of time from before the administration of collagen, estimating the variation value based upon the volume of the foot before the administration and conducting single disposal diffusion analysis. The suppressive rate was estimated from the variation value on the 19th day. As the result, the compound of Example 11 showed the suppressive rate of 24.1% in case of the administration at the dose of 10 mg/kg and 45.4% in case of that at the dose of 30 mg/kg.

(b) Therapeutic Experiment

The animals which were sensitized in the same manner as in (a) and showed crisis of arthritis on the 14th day were selected and divided into 6-animal groups. The test compound solution was orally administered once a day from the 14th day to the 27th day. The assessment of the effect was conducted by estimating the suppressive rate relative to the control group from the variation value on the 30th day based upon the volume of the foot on the 14th day. The compound of Example 11 showed the suppressive rate of 192.5% by the administration at the dose of 30 mg/kg.

PHARMACOLOGICAL EXPERIMENTAL EXAMPLE 4

Effects on mouse glomerulonephritis

The high GBM(Glomerular basement membrane)-containing fractions obtained from the renal cortex of mice were suspended in a saline in 20%, and a 1:1 emulsion with Freund's complete adjuvant (hereinafter referred to as FCA) was prepared. This emulsion (3 ml) was intracutaneously administered to rabbits at several separate sites of the depilated back. This infection was sensitized every week 5 times in total, and on the 10th day from the final sensitization, the anti-GBM serum was obtained by collecting the entire blood from the carotid artery of the rabbits. A 1:1 emulsion of a solution of rabbit immune globulin (RGG, Sigma) in saline (4 mg/ml) with FCA was prepared, and 3 ml of the emulsion was intracutaneously administered to rabbits at several separate sites in the depilated back. This sensitization was conducted weekly 5 times in total, and on the 10th day from the final sensitization, anti-GBM serum was obtained by collecting the entire blood from the carotid artery of the rabbits. A 1:1 emulsion (0.25 ml) of a solution of rabbit immune globlin (RGG, Sigma) in saline (4 mg/ml) with FCA was intraperitoneally administered to male C57Bl/6 mice (9-10 mice per group) weighing about 20 g, and mice glomerulonephritis was produced. Five days after, 0.05 ml of anti-GBM serum was intravenously administered in the vein of the tail, and the amount of the urinous protein with the lapse of time was measured. Based on the criterion, negative:0 score, trace:1 score, 30 mg/dl:2 score, 100 mg/dl:3 score, 300 mg/dl:4 score and more than 2000 mg/dl:5 score, the average scores of the respective groups were estimated. The solution of the test compound was orally administered for 15 consecutive days from the administration of the anti-GBM serum. The action was evaluated by the suppressive rate relative to the control group from the variation value on the 16th day based on the score of the urinous protein amount on the day of the administration of anti-GBM serum. As the result, the compound of Example 11 showed the suppressive rate of 35.2% at the dosage of 10 mg/kg and 92.9% at the dosage of 30 mg/kg.

PHARMACOLOGICAL EXPERIMENTAL EXAMPLE 5

Action on Experimental Allergic Cerebral Myllitis

A 40% emulsion of the guinea pig cerebral spine in 0.5% phenol solution was prepared and a 1:1 emulsion of said emulsion with Freund's complete adjuvant was prepared and injected to male Wistar rats (10 rats per group) weighing 270-330 g at the sole of both of the hindlimbs at 0.1 ml per injection. At the same time, 0.125 ml of injection of non-viable pertussis bacilli of $2 \times 10^9$ bacilli/ml was intramuscularly administered in the both femora for sensitization. The assessment of crisis of experimental allergic cerebral myllitis was conducted by the paralysis of the tail which is the initial symptom in accordance with the method of Levine et al [Arch. Int. Pharmacodyn. Ther. vol. 230, p 309 (1977)] and the result was estimated from the mean days before the onset of the symptom. The test compound solution was orally administered for 20 consecutive days from the day of the sensitization. The mean days before the onset of the symptom by the crisis was $20.5 \pm 2.30$ days when the compound of Example 11 was administered at the dosage of 30 mg/kg, whereas that of the control group was $12.0 \pm 0.35$ days. Accordingly, it was found that the compound of Example 11 significantly delayed the crysis of experimental allergic cerebral myllitis and reduced the crisis rate by 50%.

PHARMACOLOGICAL EXPERIMENTAL EXAMPLE 6

Delayed Hypersensitive Reaction-Potentiating Action

Delayed hypersensitivity was induced in accordance with the method of Uyeki [Proc. Soc. Exptl. Biol. Med., vol. 132, pp 1140-1146 (1969)]. Methylated human serum albumin antigen was prepared in accordance with the method of Crowle [J. Allergy, vol. 42, pp 140-156 (1968)]. A 0.1 ml of injection of a 0.25% solution of methylated human serum albumin was subcutaneously administered to mice (7-9 mice per group) in the back for sensitization. At one hour after the final administration of the test compound solution, a 0.025 ml of injection of a 0.1% solution of methylated human serum albumin was subcutaneously administered to mice in the sole of the left hindlimb. After 24 hours, the thickness of the limb (mm) was measured by a stereoscopic microscope of 10 magnifications in accordance with the measurement method of Baba et al [Acta Path. Jap., vol. 27, pp 165-183 (1977)]. The difference between the measurement value before and after the injection for induction of antigen was calculated, and the result was shown by the mean value and the average error and the examination of significant difference was conducted by single disposal method.

All the test compounds were dissolved or suspended in a 0.5% methyl cellulose solution to give the test compound solutions. The solutions were orally administered for 3 consecutive days from the day of the sensitization. When the compound of Example 1 was administered at the dosage of 10 mg/kg, the thickness was $0.98 \pm 0.12$ mm, and the compound potentiated delayed hypersensitivity induced by methylated human serum albumin significantly.

PHARMACEUTICAL EXPERIMENTAL EXAMPLE 7

Action on Mouse P388 Leukaemia Cell

Mouse P388 leukaemia cells ($1 \times 10^6$ cells) were intraperitoneally transplanted into male CDF 1 mice and for 5 consecutive days (once a day) from the next day of the transplantation, the test compound was intraperitoneally administered. The survival conditions of mice (6 mice per group) was observed and T/C (%) value was calculated from the mean survival time (MST) in accordance with the following formula: T/C (%)=(MST of treated group/MST of non-administered group)×100

As the result, the compound of Example 11 showed T/C of 212% at the dosage of 250 mg/kg and T/C of 245% at the dosage of 500 mg/kg.

TOXICITY TEST

When the compounds of Example 2 and 11 were orally administered to rats at the dosage of 1000 mg/kg respectively, all rats survived.

When the compounds of the formula (I) or pharmaceutically acceptable salts thereof of the present invention are used as medicaments, they can be orally or non-orally administered in forms such as powders, tablets, capsules, granules, injections, suppositories, ointments and so on in mixture with suitable carriers, excipients and diluents. While the dosage varies depending on the symptom, body weight, age and so on of a patient, for example, when they are orally administered for anti-cancer or immunosuppressive use, the daily dosage for an adult is usually 10–500 mg, which is suitably administered at one dose or several divided doses.

Below, the present invention is explained specifically by Examples, to which this invention is not limited.

EXAMPLE 1

3,4-Dihydro-3-(2-chlorophenyl)-6-chlorosulfonyl-2-methyl-4-oxothieno[2,3-d]pyrimidine To 140 ml of chlorosulfonic acid was added little by little 54.8 g of 3,4-dihydro-3-(2-chlorophenyl)-2-methyl-4-oxothieno[2,3-d]pyrimidine. After the mixture was heated at 70°–75° C. on the oil bath and stirred for 1.5 hours, the reaction mixture was cooled and then poured onto 2 l of icewater carefully. The precipitated crystals were collected by suction-filtration to afford 65 g of the title compound, m.p. 172°–174° C.

EXAMPLE 2

3,4-Dihydro-3-(2-chlorophenyl)-2-methyl-4-oxo-6-sulfamoylthieno[2,3-d]pyrimidine In 200 ml of tetrahydrofuran was suspended 23 g of 3,4-dihydro-3-(2-chlorophenyl)-6-chlorosulfonyl-2-methyl-4-oxothieno[2,3-d]pyrimidine, and this suspension was poured onto 200 ml of ammonia water at one time. The mixture was stirred at room temperature for 40 minutes. The reaction mixture was concentrated, and water was added to the residue. The crystals were collected by suction-filtration to afford 15.8 g of the title compound, m.p. 251° C.

EXAMPLE 3

3,4-Dihydro-3-(2-chlorophenyl)-2-methyl-6-(4-methyl-1-piperazinyl)sulfonyl-4-oxothieno[2,3-d]pyrimidine.-hydrochloride To 5.0 g of 3,4-dihydro-3-(2-chlorophenyl)-6-chlorosulfonyl-2-methyl-4-oxothieno[2,3-d]pyrimidine were added 80 ml of dichloromethane, 4.5 ml of triethylamine and 1.4 g of N-methylpiperazine, and the mixture was stirred at room temperature for 20 minutes. After the reaction mixture was washed with water, isopropyl alcohol saturated with hydrochloric acid gas was added to the concentrated residue to convert it into hydrochloride, which was recrystallized from methanol to afford 3.2 g of the title compound, m.p. 295°–297° C.

EXAMPLE 4

3,4-Dihydro-6-[N-(4-acetylaminobutyl)sulfamoyl]-3-(2-chlorophenyl)-2-methyl-4-oxothieno[2,3-d]pyrimidine To 8.0 g of 3,4-dihydro-3-(2-chlorophenyl)-6-chlorosulfonyl-2-methyl-4-oxothieno[2,3-d]pyrimidine were added 150 ml of dichloromethane, 3.3 g of 4-acetylaminobutylamine and 5.9 ml of triethylamine, and the mixture was stirred at room temperature for 3 hours. After the reaction mixture was washed with water, the concentrated residue was purified by means of silica gel chromatography to obtain 5.71 g of oily substance, which was crystallized from ethyl acetate-hexane to afford 4.44 g of the title compound, m.p. 203°–206° C. (decomposition).

EXAMPLE 5

3,4-Dihydro-2-bromethyl-3-(2-chlorophenyl)-4-oxo-6-sulfamoylthieno[2,3-d]pyrimidine To 105.5 g of 3,4-dihydro-3-(2-chlorophenyl)-2-methyl-4-oxo-6-sulfamoylthieno[2,3-d]pyrimidine was added 1 l of acetic acid, and bromine was added dropwise while heating in the oil bath at 100° C. over 1 hour and 15 minutes. After the reaction mixture was stirred under reflux for 2 hours, the mixture was concentrated. The residue was crystallized to afford 110 g of the title compound, m.p. 190°–192° C.

EXAMPLE 6

3,4-Dihydro-2-acetoxymethyl-3-(2-chlorophenyl)-4-oxo-6-sulfamoylthieno[2,3-d]pyrimidine To 10.5 g of 3,4-dihydro-2-bromomethyl-3-(2-chlorophenyl)-4-oxo-6-sulfamoylthieno[2,3-d]pyrimidine were added 100 ml of dimethylformamide and 6.0 g of sodium acetate, and the mixture was stirred at 80° C. for 2 hours. The reaction mixture was poured onto water, and the mixture was extracted with ethyl acetate, washed with water and concentrated to give 8.7 g of the residue. This residue was purified by silica gel column chromatography to give 5.3 g of an oily substance, which was crystallized from ethanol to afford 3.4 g of the title compound, m.p. 192.5°–194° C.

EXAMPLE 7

3,4-Dihydro-(2-chlorophenyl)-2-hydroxymethyl-4-oxo-6-sulfamoylthieno[2,3-d]pyrimidine To 9.3 g of 3,4-dihydro-2-acetoxymethyl-3-(2-chlorophenyl)-4-oxo-6-sulfamoylthieno[2,3-d]pyrimidine were added 200 ml of methanol, 30 ml of water and 14.3 ml of conc. hydrochloric acid, and the mixture was stirred under reflux for 2 hours. The reaction mixture was concentrated, and the residue was crystallized from methanol to give 6.2 g of pale yellow crystals, which was recrystallized from methanol to afford 2.6 g of the title compound, m.p. 259° C. (decomposition).

EXAMPLE 8

3,4-Dihydro-3-(2-chlorophenyl)-2-(N-propylcarbamoyloxymethyl)-4-oxo-6-sulfamoylthieno[2,3-d]pyrimidine To 1.5 g of 3,4-dihydro-3-(2-chlorophenyl)-2-hydroxymethyl-4-oxo-6-sulfamoylthieno[2,3-d]pyrimidine were added 50 ml of pyridine and 2 ml of propyl isocyanate, and the mixture was stirred at 75° C. for 1 hour. The reaction mixture was concentrated, and water was added to the residue, followed by addition of dilute hydrochloric acid for acidification. The resultant was extracted with ethyl acetate and washed with water. The concentrated residue was purified by silica gel column chromatography to give 1.9 g of an oily substance, which was crystallized from ethanol to afford 1.1 g of the title compound, m.p. 169°–170° C. (decomposition).

EXAMPLE 9

3,4-Dihydro-(2-chlorophenyl)-2-(4-methyl-1-piperazinylmethyl)-4-oxo-6-sulfamoylthieno[2,3-d]pyrimidine To 5.0 g of 3,4-dihydro-2-bromomethyl-3-(2-chlorophenyl)-4-oxo-6-sulfamoylthieno[2,3-d]pyrimidine were added 50 ml of dimethylformamide, 1.5 g of N-methylpiperazine and 3.2 g of potassium carbonate, and the mixture was stirred at 40° C. for 1.5 hours. The reaction mixture was poured onto water, and the mixture was extracted with ethyl acetate. The concentrated residue of the extract was crystallized from ethanol, followed by recrystallization of the obtained crystals from methanol-chloroform to afford 1.9 g of the title compound, m.p. 233.5°–234° C. (decomposition). The hydrochloric thereof showed m.p. of 246°–247° C. (decomposition).

EXAMPLE 10

3,4-Dihydro-6-[N-(4-acetylaminobutyl)sulfamoyl]-3-(2-chlorophenyl)-2-(4-ethyl-1-piperazinylmethyl)-4-oxothieno[2,3-d]pyrimidine.hydrochloride To 3 g of 3,4-dihydro-6-[N-(4-acetylaminobutyl)sulfamoyl]-3-(2-chlorophenyl)-2-methyl-4-oxothieno[2,3-d]pyrimidine was added 50 ml of acetic acid, and 1.23 g of bromine dissolved in 2 ml of acetic acid was added dropwise to the mixture at 100°–110° C. over 40 minutes. After stirring at 105° C. for 4 hours, the reaction mixture was concentrated to give 4.24 g of the residue. To this residue were added 30 ml of dimethylformamide, 1.1 g of N-ethylpiperazine and 1 g of potassium carbonate, and the mixture was stirred at room temperature for 6 hours. The reaction mixture was poured onto water and the mixture was extracted with chloroform. The concentrated residue was purified by silica gel column chromatography to give 3.1 g of an oily substance, which was converted into its hydrochloride by ethanol saturated with hydrochloric acid gas. The hydrochloride was crystallized from acetone-methanol-ethanol, followed by recrystallization of the crystals to give 0.40 g of the title compound, m.p. 160°–165° C.

EXAMPLE 11

3,4-Dihydro-3-(2-chlorophenyl)-2-(4-ethyl-1-piperazinylmethyl)-4-oxo-6-sulfamoylthieno[2,3-d]pyrimidine To 3 g of 3,4-dihydro-2-bromomethyl-3-(2-chlorophenyl)-4-oxo-6-sulfamoylthieno[2,3-d]pyrimidine were added 40 ml of dimethylformamide, 0.8 ml of 1-ethylpiperazine and 2.7 g of potassium carbonate, and the mixture was stirred at room temperature for 1 hour. The reaction mixture was poured onto water, and the mixture was extracted with chloroform. The concentrated residue was purified by silica gel column chromatography, crystallized from ethyl acetate and recrystallized from ethanol to give 320 mg of the title compound, m.p. 203°–204° C. (decomposition).

EXAMPLE 12

3,4-Dihydro-3-(2-chlorophenyl)-2-(4-ethyl-1-piperazinylmethyl)-5,6-dimethyl-4-oxothieno[2,3-d]pyrimidine In 300 ml of chloroform was dissolved 15.0 g of 3,4-dihydro-2-chloromethyl-3-(2-chlorophenyl)-4-5,6-dimethyloxothieno[2,3-d]pyrimidine, and 5.8 g of potassium carbonate was added thereto. Further, 5.8 g of 1-ethylpiperazine was added dropwise thereto, and the mixture was heated under reflux for 4 hours. The reaction mixture was filtered, and the filtrate was concentrated under reduced pressure. The obtained oily substance was subjected to silica gel column chromatography to give 7.0 g of the title compound as pale yellow crystals of m.p. 126°–129° C. This compound was converted into its hydrochloride with a hydrochloric acid-methanol solution, which was recrystallized to give 4 g of 2 hydrochloride of the title compound, m.p. 263°–265° C. (decomposition).

EXAMPLE 13

3,4,5,6,7,8-Hexahydro-3-(2-chlorophenyl)-2-(4-ethyl-1-piperazinylmethyl)-4-oxo(1)benzothieno[2,3-d]pyrimidine In 40 ml of chloroform was dissolved 820 mg of 3,4,5,6,7,8-hexahydro-2-chloromethyl-3-(2-chlorophenyl)-4-oxo(1)-benzothieno[2,3-d]pyrimidine, and 300 mg of potassium carbonate was added. Further, 310 mg of 1-ethylpiperazine was added dropwise. The mixture was heated under reflux for 5 hours. The reaction mixture was filtered, and the filtrate was concentrated under reduced pressure to give an oily substance, which was purified by silica gel chromatography. The obtained white crystals were recrystallized from ethanol to give 680 mg of the title compound, m.p. 140°–142° C.

EXAMPLE 14

3,4-Dihydro-3-(2-chlorophenyl)-6-ethoxycarbonyl-2-(4-ethyl-1-piperazinylmethyl)-5-methyl-4-oxothieno[2,3-d]pyrimidine.¼ hydrate To a mixture of 16.7 g of ethyl acetoacetate, 25 g of N-(2-chlorophenyl)cyanoacetamide, 4 g of sulfur and 100 ml of ethanol was added 20 ml of morpholine at room temperature under stirring, and the mixture was stirred at 50° C. for 6 hours. After the sulfur remaining in the reaction mixture was filtered off, the filtrate was left standing at room temperature overnight. The precipitated crystals were collected by filtration to give 9.49 g of N-(2-chlorophenyl)-2-amino-5-ethoxycarbonyl-4-methylthiophene-3-carboxamide. This compound was dissolved in 100 ml of acetic acid, whereto 6.35 ml of chloroacetyl chloride was added. The mixture was refluxed for 1 hour. The reaction mixture was poured onto ice-water, and the precipitated crystals were collected by filtration, and dried at 80° C. for 30 minutes to give 10 g of N-(2-chlorophenyl)-2-chloroacetylamino-5-ethoxycarbonyl-4-methylthiophene-3-carboxamide.

This chloroacetylamino compound was dissolved in 120 ml of phosphorus oxychloride, and the solution was refluxed for 10 hours. The reaction mixture was poured onto ice-water, and the precipitated crystals were collected by filtration, dissolved in chloroform, and dried over anhydrous sodium sulfate. Thereafter, chloroform was distilled off, and the residue was crystallized from hexane-ethyl acetate to give 2.9 g of 3,4-dihydro-2-chloromethyl-3-(2-chlorophenyl)-6-ethoxycarbonyl-5-methyl-4-oxothieno[2,3-d]pyrimidine.

The crystals were dissolved in 15 ml of chloroform, whereto 2 g of sodium hydrogencarbonate and 1.5 ml of 1-ethylpiperazine were added. The mixture was stirred at 60° C. for 3 hours. After the reaction mixture was washed with water and dried over anhydrous sodium sulfate, chloroform was distilled off. The residue was purified by silica gel column chromatography, crystallized from hexane-ethyl acetate and recrystallized from the same solvent to give 0.4 g of the title compound, m.p. 135°–138° C. (decomposition).

EXAMPLE 15

3,4-Dihydro-3-(2-chlorophenyl)-6-ethyl-2-(4-ethyl-1-piperazinylmethyl)-4-oxothieno[2,3-d]pyrimidine.2 hydrochloride In 30 ml of chloroform was dissolved 1.0 g of 3,4-dihydro-2-chloromethyl-3-(2-chlorophenyl)-6-ethyl-4-oxothieno[2,3-d]pyrimidine, and 0.50 g of potassium carbonate and 0.55 ml of 1-ethylpiperazine were added to the solution. The mixture was stirred at 50° C. for 2 hours. After the reaction mixture was washed with water and dried over anhydrous sodium sulfate, chloroform was distilled off. The residue was purified by silica gel column chromatography and the thus obtained oily substance was crystallized from hydrochloric acid-methanol, followed by recrystallization of the crystals from methanol-ethanol to give 0.58 g of the title compound, m.p. 240°–244° C. (decomposition).

EXAMPLE 16

3,4-dihydro-6-bromo-3-(2-chlorophenyl)-2-(4-ethyl-1-piperazinylmethyl)-4-oxothieno[2,3-d]pyrimidine In chloroform was dissolved 22.85 g of 3,4-dihydro-3-(2-chlorophenyl)-2-methyl-4-oxothieno[2,3-d]pyrimidine, and 19.5 g of N-bromosuccinimide and trace benzoyl peroxide were added to the solution. The mixture was refluxed for 10 hours. After the resulting crystals were removed from the reaction mixture, the solvent was distilled off. The residue was crystallized from hexane-ethyl acetate to give 22.95 g of 3,4-dihydro-6-bromo-3-(2-chlorophenyl)-2-methyl-4-oxothieno[2,3-d]pyrimidine, m.p. 164.5°–166.5° C.

To 15 g of 3,4-dihydro-6-bromo-3-(2-chlorophenyl)-2-methyl-4-oxothieno[2,3-d]pyrimidine was added 100 ml of acetic acid, and while the mixture was stirred under reflux, 6.75 g of bromine was added dropwise slowly. After acetic acid was distilled off, the residue was crystallized from ethanol to give 13.87 g of crystals. The crystals were dissolved in 10 ml of dimethylformamide, whereto 3 g of potassium carbonate and 6 ml of 1-ethylpiperazine were added. The mixture was stirred at room temperature for 15 minutes. The reaction mixture was diluted with chloroform, washed with water and dried over anhydrous sodium sulfate. After chloroform was distilled off, the residue was purified by silica gel column chromatography to give 3.4 g of an oily substance, which was crystallized from hexane-ethyl acetate and recrystallized from the same solvent to give 750 mg of the title compound, m.p. 155°–157.5° C.

EXAMPLE 17

3,4-Dihydro-3-(2-chloro-4-nitrophenyl)-2-(4-ethyl-piperazinyl-1-methyl)-6-nitro-4-oxothieno[2,3-d]pyrimidine.2 hydrochloride.½ hydrate To a mixture of 100 ml of fuming sulfuric acid and 100 ml of sulfuric acid was added 9.56 g of 3,4-dihydro-3-(2-chlorophenyl)-2-methyl-4-oxothieno[2,3-d]pyrimidine under ice-cooling, and the mixture was left standing under ice-cooling for 30 minutes, and thereafter the temperature of the mixture was gradually elevated to room temperature. The mixture was stirred at room temperature for 1 hour. The reaction mixture was poured onto ice-water and the resulting crystals were collected by filtration. The obtained crystals were dissolved in chloroform, washed with an aqueous solution of sodium hydrogencarbonate and dried over anhydrous sodium sulfate. The solvent was distilled off. The residue was crystallzed from methanol-ethyl acetate to give 10.8 g of 3,4-dihydro-3-(2-chloro-4-nitrophenyl)-2-methyl-6-nitro-4-oxothieno[2,3-d]pyrimidine, m.p. 166°–168° C.

To 5 g of 3,4-dihydro-3-(2-chloro-4-nitrophenyl)-2-methyl-6-nitro-4-oxothieno[2,3-d]pyrimidine was added 50 ml of acetic acid. With stirring under reflux, 2.8 g of bromine was added dropwise, and after the dropwise addition, the mixture was stirred under reflux for 1 hour. The reaction mixture was concentrated. The residue was crystallized from ethanol to give 5.65 g of 3,4-dihydro-2-bromomethyl-3-(2-chloro-4-nitrophenyl)-2-methyl-6-nitro-4-oxothieno[2,3d]pyrimidine.

In chloroform was dissolved 5.6 g of 3,4-dihydro-2-bromomethyl-3-(2-chloro-4-nitrophenyl)-2-methyl-6-nitro-4-oxothieno[2,3-d]pyrimidine, whereto 2.3 g of sodium hydrogen carbonate and 2.1 ml of 1-ethylpiperazine were added. The mixture was stirred under reflux for 5 hours. The reaction mixture was washed with water, dried over anhydrous sodium sulfate and concentrated. The residue was purified by silica gel column chromatography and the obtained oily substance was converted into hydrochloride by adding hydrochloric acid-methanol, and the hydrochloride was recrystallized from methanol to give 0.13 g of the title compound of m.p. of not less than 320° C.

EXAMPLE 18

3,4-Dihydro-3-(2-chlorophenyl)-2-ethyl-4-oxo-6-sulfamoylthieno[2,3-d]pyrimidine

To 10 ml of chlorosulfonic acid was added little by little 3.14 g of 3,4-dihydro-3-(2-chlorophenyl)-2-ethyl-4-oxothieno[2,3-d]pyrimidine at room temperature. The mixture was heated on an oil bath at 70°–75° C., and stirred for 1.5 hours. Thereafter, the reaction mixture was cooled, and poured onto ice-water. The resulting crystals were suction-filtered. The crystals were suspended in 20 ml of tetrahydrofuran, and the suspension was poured onto 30 ml of ammonia water. The mixture was stirred at room temperature for 30 minutes. The reaction mixture was concentrated. The residue was purified by silica gel column chromatography, crystallized from hexane-ethyl acetate and recrystallized from ethyl acetate-methanol to give 237 mg of the title compound, m.p. 253° C.

In the same manner as in the foregoing Examples, the compounds of Examples 19–58 as shown in Table 2 can be produced.

TABLE 2

| Example No. | A | R¹ | R² | R³ | R⁴ | R⁵ | R⁶ | m.p. (°C.) |
|---|---|---|---|---|---|---|---|---|
| 19 | CH₂ | H | H | 3-Cl | H | H | SO₂NH₂ | 244-245 |
| 20 | CH₂ | H | H | 4-Cl | H | H | SO₂NH₂ | 247 |
| 21 | CH₂ | H | 3-Cl | 2-Cl | H | H | SO₂NH₂ | 141-143 |
| 22 | CH₂ | H | H | 2-Cl | H | H | SO₂N(piperazinyl-NCH₂CH=CHPh) | 240-241 hydrochloride |
| 23 | CH₂ | H | H | 2-Cl | H | H | SO₂NHCH₂CH₂-(3,4-dimethoxyphenyl) | 156-159 |
| 24 | CH₂ | H | H | 2-Cl | H | H | SO₂N(piperazinyl-NCH₃) | 210-211 |
| 25 | CH₂ | H | H | 2-Cl | H | H | SO₂N(piperazinyl-NCH₂CH₃) | 145-147 |
| 26 | CH₂ | H | H | 2-Cl | H | H | SO₂NH(CH₂)₂NHCOCH₃ | 193-195 |
| 27 | CH₂ | H | H | 2-Cl | H | H | SO₂NH(CH₂)₄NHCOCH₃ | 204-207 |
| 28 | CH₂ | H | H | 2-Cl | H | H | SO₂NH(CH₂)₆NHCOCH₃ | 119-120 |
| 29 | CH₂ | OCONHCH₃ | H | 2-Cl | H | H | SO₂NH₂ | 213.5-215.0 (decomp.) |
| 30 | CH₂ | OCONHPh | H | 2-Cl | H | H | SO₂NH₂ | 145-146 (decomp.) |

TABLE 2-continued
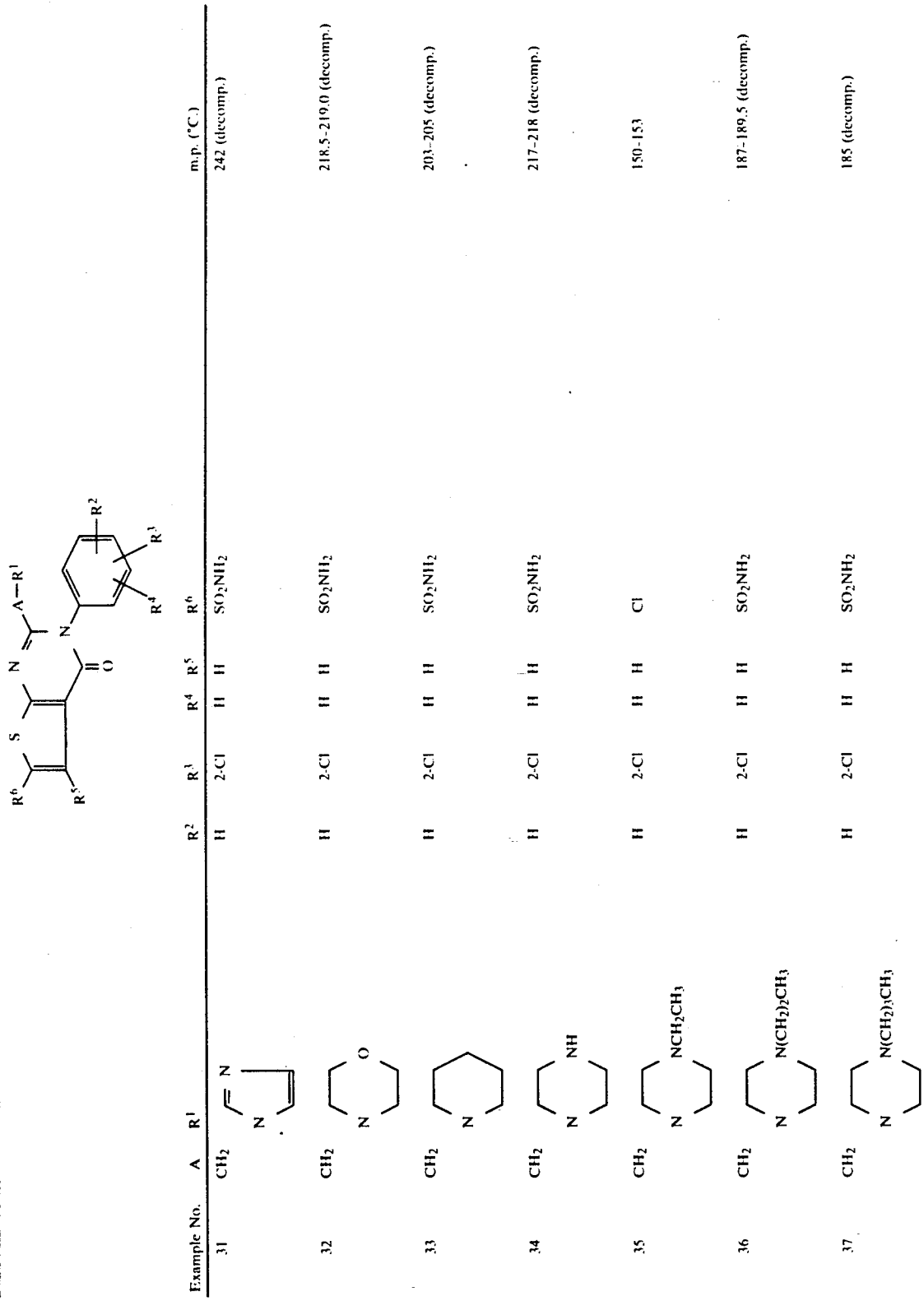
| Example No. | A | R¹ | R² | R³ | R⁴ | R⁵ | R⁶ | m.p. (°C.) |
|---|---|---|---|---|---|---|---|---|
| 31 | CH₂ | (imidazole) | H | 2-Cl | H | H | SO₂NH₂ | 242 (decomp.) |
| 32 | CH₂ | (morpholine) | H | 2-Cl | H | H | SO₂NH₂ | 218.5–219.0 (decomp.) |
| 33 | CH₂ | (piperidine) | H | 2-Cl | H | H | SO₂NH₂ | 203–205 (decomp.) |
| 34 | CH₂ | (piperazine-NH) | H | 2-Cl | H | H | SO₂NH₂ | 217–218 (decomp.) |
| 35 | CH₂ | (N-ethyl piperazine) NCH₂CH₃ | H | 2-Cl | H | H | Cl | 150–153 |
| 36 | CH₂ | N(CH₂)₂CH₃ piperazine | H | 2-Cl | H | H | SO₂NH₂ | 187–189.5 (decomp.) |
| 37 | CH₂ | N(CH₂)₃CH₃ piperazine | H | 2-Cl | H | H | SO₂NH₂ | 185 (decomp.) |

TABLE 2-continued

| Example No. | A | R¹ | R² | R³ | R⁴ | R⁵ | R⁶ | | m.p. (°C.) |
|---|---|---|---|---|---|---|---|---|---|
| 38 | $CH_2$ | piperazine-N($CH_2)_5CH_3$ | H | 2-Cl | H | H | $SO_2NH_2$ | | 149-151 (decomp.) |
| 39 | $CH_2$ | piperazine-N$CH_2CH=CH$-phenyl | H | 2-Cl | H | H | $SO_2NH_2$ | fumarate | 216-217 (decomp.) |
| 40 | $CH_2$ | piperazine-N-$CH_2$-phenyl | H | 2-Cl | H | H | $SO_2NH_2$ | | 216-217 (decomp.) |
| 41 | $CH_2$ | piperazine-N-(2-pyridyl) | H | 2-Cl | H | H | $SO_2NH_2$ | | 178-180 (decomp.) |
| 42 | $CH_2$ | piperazine-NCHO | H | 2-Cl | H | H | $SO_2NH_2$ | | 242-243 (decomp.) |
| 43 | $CH_2$ | piperazine-N($CH_2)_2OH$ | H | 2-Cl | H | H | $SO_2NH_2$ | | 197-199 (decomp.) |

TABLE 2-continued

| Example No. | A | R¹ | R² | R³ | R⁴ | R⁵ | R⁶ | m.p. (°C.) |
|---|---|---|---|---|---|---|---|---|
| 44 | $CH_2$ | piperazine-NCH₃ | H | 3-Cl | H | H | $SO_2NH_2$ | 195 (decomp.) |
| 45 | $CH_2$ | piperazine-NCH₃ | H | 4-Cl | H | H | $SO_2NH_2$ | 161 (decomp.) |
| 46 | $CH_2$ | piperazine-NCH₃ | 3-Cl | 2-Cl | H | H | $SO_2NH_2$ | 225-226 (decomp.) |
| 47 | $CH_2$ | piperazine-NCH₃ | H | 2-F | H | H | $SO_2NH_2$ | 229 (decomp.) |
| 48 | $CH_2$ | piperazine-NCH₃ | H | 2-CF₃ | H | H | $SO_2NH_2$ | 230-232 (decomp.) |
| 49 | $CH_2$ | Br | H | 2-Cl | H | H | $NH(CH_2)_2NHCOCH_3$ | 192-197 (decomp.) |
| 50 | $CH_2$ | Br | H | 3-Cl | H | H | $SO_2NH_2$ | 224-227 (decomp.) |
| 51 | $CH_2$ | Br | 3-Cl | 2-Cl | H | H | $SO_2NH_2$ | 203-205 (decomp.) |
| 52 | $CH_2$ | piperidine-NCH₃ | H | 2-Cl | H | H | $SO_2N(C_2H_5)_2$ | 189-189.5 (decomp.) |

TABLE 2-continued

![structure: R6-thiophene(R5,R4)-C(=O)-N(CH-A-R1)-phenyl(R2,R3,R4,R6)]

| Example No. | A | R¹ | R² | R³ | R⁴ | R⁵ | R⁶ | m.p. (°C.) |
|---|---|---|---|---|---|---|---|---|
| 53 | $CH_2$ | piperazine-NCH₃ | H | 2-Cl | H | H | $SO_2NHC_2H_5$ | 190-191 (decomp.) |
| 54 | $CH_2$ | piperazine-NCH₃ | H | H | H | H | $SO_2NH_2$ | 214-215 (decomp.) |
| 55 | $CH_2$ | piperidine-CH₂CH₃ | H | H | H | H | $SO_2NH_2$ | 203-204 (decomp.) |
| 56 | $CH_2$ | H | H | 2-Cl | H | H | $SO_2NHC_2H_5$ | 194-195 |
| 57 | $CH_2$ | H | H | 2-Cl | H | H | $SO_2N(C_2H_5)_2$ | 109-110 |
| 58 | $CH_2$ | morpholine | H | 2-Cl | H | $CH_3$ | $CO_2CH_2CH_3$ | 102-105 |

In the same manner as in Examples mentioned above, the following compounds can be produced.

3,4-Dihydro-3-(2-fluorophenyl)-2-cyclohexylcarbonyloxymethyl-4-oxo-6-sulfamoylthieno[2,3-d]pyrimidine
3,4-Dihydro-2-benzoyloxymethyl-3-(2-fluorophenyl)-4-oxo-6-sulfamoylthieno[2,3-d]pyrimidine
3,4-Dihydro-3-(2-fluorophenyl)-2-[(4-(2-froyl)-1-piperazinyl)methyl]-4-oxo-6-sulfamoylthieno[2,3-d]pyrimidine
3,4-Dihydro-3-(2-cyanophenyl)-2-[(4-methyl-1-piperazinyl)methyl]-4-oxo-6-sulfamoylthieno[2,3-d]pyrimidine
3,4-Dihydro-2-[(4-methyl-1-piperazinyl)methyl]-3-(2-nitrophenyl)-4-oxo-6-sulfamoylthieno[2,3-d]pyrimidine
3,4-Dihydro-3-(2-fluorophenyl)-6-(1-imidazolyl)sulfonyl-2-[(4-methyl-1-piperazinyl)methyl]-4-oxothieno[2,3-d]pyrimidine
3,4-Dihydro-2-[(4-(4-ethoxybenzoyl)-1-piperazinyl)methyl]-4-oxo-3-phenyl-6-sulfamoylthieno[2,3-d]pyrimidine
3,4-Dihydro-3-(2-aminophenyl)-2-[(4-methyl-1-piperazinyl)methyl]-6-sulfamoylthieno[2,3-d]pyrimidine
3,4-Dihydro-3-(2,4-dimethoxyphenyl)-2-[(4-methyl-1-piperazinyl)methyl]-4-oxo-6-sulfamoylthieno[2,3-d]pyrimidine
3,4-Dihydro-2-[(4-ethyl-1-piperazinyl)methyl]-4-oxo-6-sulfamoyl-3-(2-trifluoromethylphenyl)thieno[2,3-d]pyrimidine
3,4-Dihydro-2-[(4-ethyl-1-piperazinyl)methyl]-4-oxo-6-piperidinosulfonyl-3-(2-trifluoromethylphenyl)-thieno[2,3d]pyrimidine
3,4-Dihydro-2-[(4-ethyl-1-piperazinyl)-methyl]-6-morpholinosulfonyl- 4-oxo-3-(2-trifluoromethylphenyl)-thieno[2,3-d]pyrimidine
3,4-Dihydro-2-methyl-4-oxo-3-phenyl-6-sulfamoylthieno[2,3-d]pyrimidine
3,4-Dihydro-3-(2-fluorophenyl)-2-methyl-4-oxo-6-sulfamoylthieno[2,3-d]pyrimidine
3,4-Dihydro-3-(2-methoxyphenyl)-2-methyl-4-oxo-6-sulfamoylthieno[2,3-d]pyrimidine
3,4-Dihydro-2-methyl-4-oxo-6-sulfamoyl-3-(2-trifluoromethylphenyl)thieno[2,3-d]pyrimidine
3,4-Dihydro-2-methyl-3-(2-nitrophenyl)-4-oxo-6-sulfamoylthieno[2,3-d]pyrimidine
3,4-Dihydro-2-methyl-4-oxo-6-sulfamoyl-3-(2-methylphenyl)thieno[2,3-d]pyrimidine
3,4-Dihydro-3-(2,4-dichlorophenyl)-2-methyl-4-oxo-6-sulfamoylthieno[2,3-d]pyrimidine
3,4-Dihydro-3-(2,5-dichlorophenyl)-2-methyl-4-oxo-6-sulfamoylthieno[2,3-d]pyrimidine
3,4-Dihydro-3-(2,6-dichlorophenyl)-2-methyl-4-oxo-6-sulfamoylthieno[2,3-d]pyrimidine
3,4-Dihydro-3-(2-aminophenyl)-2-methyl-4-oxo-6-sulfamoylthieno[2,3-d]pyrimidine
3,4-Dihydro-3-(2-hydroxyphenyl)-2-methyl-4-oxo-6-sulfamoylthieno[2,3-d]pyrimidine
3,4-Dihydro-3-(2-chlorophenyl)-2-methyl-6-(N-methylsulfamoyl)-4-oxothieno[2,3-d]pyrimidine
3,4-Dihydro-3-(2-chlorophenyl)-6-(N,N-dimethylsulfamoyl)-2-methyl-4-oxothieno[2,3-d]pyrimidine
3,4-Dihydro-3-(2-chlorophenyl)-2-methyl-4-oxo-6-piperidinosulfonylthieno[2,3-d]pyrimidine
3,4-Dihydro-3-(2-chlorophenyl)-2-methyl-4-oxo-6-(1-pyrrodinyl)sulfonylthieno[2,3-d]pyrimidine
3,4-Dihydro-3-(2-chlorophenyl)-2-methyl-6-(morpholinosulfonylthieno[2,3-d]pyrimidine
3,4-Dihydro-3-(2-chlorophenyl)-2-ethyl-4-oxo-6-sulfamoylthieno[2,3-d]pyrimidine
3,4-Dihydro-3-(2-chlorophenyl)-4-oxo-2-propyl-6-sulfamoylthieno[2,3-d]pyrimidine
3,4-Dihydro-2-butyl-3-(2-chlorophenyl)-4-oxo-6-sulfamoylthieno[2,3-d]pyrimidine
3,4-Dihydro-3-(2-chlorophenyl)-2-hexyl-4-oxo-6-sulfamoylthieno[2,3-d]pyrimidine
3,4-Dihydro-2-benzyl-3-(2-chlorophenyl)-4-oxo-6-sulfamoylthieno[2,3-d]pyrimidine
3,4-Dihydro-3-(2-chlorophenyl)-2-ethyl-6-(N-ethylsulfamoyl)-4-oxothieno[2,3-d]pyrimidine
3,4-Dihydro-3-(2-chlorophenyl)-2-ethyl-6-(N,N-diethylsulfamoyl)-4-oxothieno[2,3-d]pyrimidine
3,4-Dihydro-2-benzyl-3-(2-chlorophenyl)-6-(N-ethylsulfamoyl)-4-oxothieno[2,3-d]pyrimidine
3,4-Dihydro-2-benzyl-3-(2-chlorophenyl)-6-(N,N-diethylsulfamoyl)-4-oxothieno[2,3-d]pyrimidine This invention has been described in detail by the specification and the examples included therein, which can be changed and modified within the spirit and the scope of the present invention.

We claim:

1. A 3,4-dihydrothieno[2,3-d]pyrimidine compound of the formula wherein A represents a straight or branched alkylene having 1 to 4 carbon atoms; $R^1$ represents $—N(R^7)(R^8)$ wherein $R^7$ and $R^8$, together with the adjacent nitrogen atom, form a piperizine ring with $>N-R^9$, wherein $R^9$ represents an alkyl having 1 to 6 carbon atoms; a cycloalkyl having 3 to 6 carbon atoms, phenyl or phenyl substituted by a halogen or an alkoxy having 1 to 4 carbon atoms; $R^2$, $R^3$ and $R^4$ may be the same or different and respectively represent hydrogen, a halogen, hydroxy, an alkyl having 1 to 4 carbon atoms, an alkyl having 1 to 4 carbon atoms substituted by a halogen, an alkoxy having 1 to 4 carbon atoms, nitro, cyano or $—N(R^{10})(R^{11})$ wherein $R^{10}$ and $R^{11}$ may be the same or different and respectively represent hydrogen, an alkyl having 1 to 4 carbon atoms, an alkanoyl having 2 to 5 carbon atoms, benzoyl or benzoyl substituted by a halogen, $R^5$ represents hydrogen, and $R^6$ represents $—SO_2NH_2$, or a pharmaceutically acceptable salt thereof.

2. The compound:
3,4-dihydro-3-(2-chlorophenyl)-2-(4-ethyl-1-piperazinyl)methyl-4-oxo-6-sulfamoylthieno[2,3-d]pyrimidine; 3,4-dihydro-3-(2-fluorophenyl)-2-(4-methyl-1-piperazinyl)methyl-4-oxo-6-sulfamoylthieno[2,3-d]pyrimidine; or 3,4-dihydro-3-(2-chlorophenyl)-2-(4-methyl-1-piperazinyl)methyl-4-oxo-6-sulfamoylthieno[2,3-d]pyrimidine, and pharmaceutically acceptable salts and hydrates thereof.

3. A pharmaceutical composition for treating chronic articular rheumatism which contains. as the active ingredient, a compound of the formula

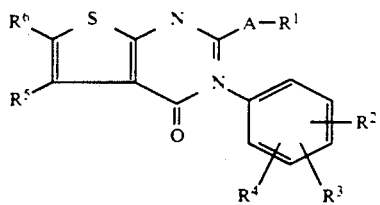

wherein A represents a straight or branched alkylene having 1 to 4 carbon atoms; $R^1$ represents $-N(R^7)(R^8)$ wherein $R^7$ and $R^8$, together with the adjacent nitrogen atom, form a piperazine ring with $>N-R^9$, wherein $R^9$ represents an alkyl having 1 to 6 carbon atoms; a cycloalkyl having 3 to 6 carbon atoms; phenyl or phenyl substituted by a halogen or an alkoxy having 1 to 4 carbon atoms; $R^2$, $R^3$ and $R^4$ may be the same or different and respectively represent hydrogen, a halogen, hydroxy, an alkyl having 1 to 4 carbon atoms, an alkyl having 1 to 4 carbon atoms substituted by a halogen, an alkoxy having 1 to 4 carbon atoms, nitro, cyano or $-N(R^{10})(R^{11})$ wherein $R^{10}$ and $R^{11}$ may be the same or different and respectively represent hydrogen, an alkyl having 1 to 4 carbon atoms, an alkanoyl having 2 to 5 carbon atoms, benzoyl or benzoyl substituted by a halogen; $R^5$ represents hydrogen, and $R^6$ represents $-SO_2NH_2$, or a pharmaceutically acceptable salt thereof.

* * * * *